(12) United States Patent
Shevchenko et al.

(10) Patent No.: US 6,375,829 B1
(45) Date of Patent: Apr. 23, 2002

(54) METHOD AND APPARATUS FOR MEASURING SCALING CAPACITY OF CALCIUM OXALATE SOLUTIONS USING AN ELECTROCHEMICALLY CONTROLLED PH CHANGE IN THE SOLUTION PROXIMATE TO A PIEZOELECTRIC MICROBALANCE

(75) Inventors: Sergey M. Shevchenko, Lisle; Dmitri L. Kouznetsov; Prasad Y. Duggirala, both of Naperville, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/519,688

(22) Filed: Mar. 7, 2000

(51) Int. Cl.$^7$ .......................... G01N 27/42; G01N 27/00
(52) U.S. Cl. .................... 205/793.5; 205/794; 204/434; 73/61.62; 73/61.75
(58) Field of Search ................................ 204/433, 434; 205/793.5, 795.5, 794; 73/61.62, 61.49, 580, 649, 61.75, 91.79, 64.53; 422/68.1, 69, 79; 436/3, 128

(56) References Cited

U.S. PATENT DOCUMENTS

| | | | | |
|---|---|---|---|---|
| 4,466,861 A | * | 8/1984 | Hultman et al. | 162/38 |
| 5,201,215 A | | 4/1993 | Granstaff et al. | |
| 5,233,261 A | * | 8/1993 | Wajid | 310/364 |
| 6,053,032 A | * | 4/2000 | Kraus et al. | 73/61.62 |

FOREIGN PATENT DOCUMENTS

EP   673 637 A1   3/1995

OTHER PUBLICATIONS

Gabrielli et al "Quartz Crystal Microbalance Investigation of Electrochemical Calcium Carbonate Scaling", J. Electrochem. Soc. 145, pp. 2386–2396, Month N/A 1998.*

Khalil et al "Water Scaling Tendency Charcterization by Coupling Constant Potential Chronoamperometry with Quartz Crystal Microbalance", C.R. Acad. Sci. Paris, 314, series II, pp. 145–149, Month N/A 1992.*

J. Ji et al., Journal of Applied Electrochemistry, 25, 642–650 (1995), Month N/A.

* cited by examiner

Primary Examiner—Jill Warden
Assistant Examiner—Kaj K. Olsen
(74) Attorney, Agent, or Firm—Michael B. Martin; Thomas M. Breininger

(57) ABSTRACT

This invention is directed to a method and apparatus for measuring the rate of calcium oxalate scale formation in a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is measured using a pH measuring module and is controlled electrochemically at from about 3.5 to about 9 and wherein the working electrode is coated with or made of a conductive material on which the intensive evolution of hydrogen gas proceeds at potentials more negative than those necessary to achieve a pH of 3.5–9 proximate to the microbalance.

23 Claims, 5 Drawing Sheets

METHOD AND APPARATUS FOR MEASURING SCALING CAPACITY OF CALCIUM OXALATE SOLUTIONS USING AN ELECTROCHEMICALLY CONTROLLED PH CHANGE IN THE SOLUTION PROXIMATE TO A PIEZOELECTRIC MICROBALANCE

TECHNICAL FIELD

This invention relates to a method and apparatus for measuring the calcium oxalate scale forming propensity of fluids and the effectiveness of calcium oxalate scale inhibitors. More specifically, this invention concerns a method of measuring the rate of calcium oxalate scale deposition on to the surface of a piezoelectric microbalance immersed in the fluid where the scale deposition is driven by an electrochemically controlled pH change in the vicinity of the microbalance.

BACKGROUND OF THE INVENTION

Calcium oxalate scale is a persistent problem in a variety of industrial processes involving water, such as pulp bleaching and sugar production. The calcium oxalate scale may remain suspended in the water or form hard deposits that accumulate on the surface of any material that contacts the water. This accumulation prevents effective heat transfer, interferes with fluid flow, facilitates corrosive processes, and harbors bacteria.

A primary detrimental effect associated with scale formation and deposition is the reduction of the capacity or bore of receptacles and conduits employed to store and convey the water. In the case of conduits used to convey scale-contaminated water, the impedance of flow resulting from scale deposition is an obvious consequence.

However, a number of equally consequential problems arise from utilization of scale-contaminated water. For example, scale deposits on the surfaces of storage vessels and conveying lines for process water may break loose and become entrained in and conveyed by the process water to damage and clog equipment through which the water is passed, e.g., tubes, valves, filters arid screens. In addition, these deposits may appear in, and detract from, the final product derived from the process, such as paper formed from an aqueous suspension of pulp.

Furthermore, when the scale-contaminated water is involved in a heat exchange process, as either the "hot" or "cold" medium, scale will be formed upon the heat exchange surfaces contacted by the water. Such scale formation forms an insulating or thermal opacifying barrier that impairs heat transfer efficiency as well as impeding flow through the system. Thus, scale formation is an expensive problem in many industrial water systems, causing delay and expense resulting from shutdowns for cleaning and removal of the deposits.

Calcium oxalate scale in biological fluids is another significant problem. In particular, kidney stones are formed of calcium oxalate, and urine analysis for calcium oxalate precipitation are used to assess the susceptibility of a patient to kidney stone formation and to monitor and screen pharmaceutical remedies.

Accordingly, there is an ongoing need for the development of new agents that prevent or inhibit the formation of calcium oxalate scales in fluids and for convenient methods of measuring the effectiveness of these inhibitors. In addition, as natural inhibitors may already be present in the solutions of interest, there is a need for effective methods of characterizing the tendency of industrial and biological solutions as such to form calcium oxalate deposits.

The effectiveness of these calcium oxalate scale inhibitors is manifested by their ability to suppress crystal growth through blocking active sites of potential centers of crystallization and preventing the agglomeration of growing crystals.

Common to the above processes is that they occur at the solid-liquid interface. Therefore the in situ measurement of the rate of crystal growth in the presence calcium oxalate scale inhibitors at the solid-liquid interface is of particular interest. Traditional measurements mostly relate to the change of the bulk properties of a test solution such as solubility, conductivity, turbidity and the like following crystal formation. There exist only a few methods for measuring crystal growth rate, and even fewer methods for conducting the measurements in situ at the solid-liquid interface.

Methods for measuring crystal growth rate at the solid-liquid interface that utilize a piezoelectric microbalance are disclosed in U.S. Pat. Nos. 5,201,215 and 6,250,140 and European Patent Application No. 676 637 A1. The principle of piezoelectric mass measurement is based upon the property of a quartz resonator to change its mechanical resonance frequency $f_0$ proportionally to the mass and viscoelastic properties of the deposited material. The change in frequency is expressed as follows:

$$\Delta f \approx -\frac{2f_0^2}{N(\mu_\mu \rho_q)1/2}\left[\rho_s + \left(\frac{\rho\eta}{4\pi f_0}\right)^{1/2}\right] \quad (6)$$

where $f_0$ is the unperturbed resonant frequency of the quartz crystal; N is the harmonic number; $\mu_\mu$ is the quartz shear stiffness, $\rho_q$ is the density of quartz; $\rho_s$ is the surface mass density of the deposit (mass/area), $\rho$ is the density of the medium contacting the resonator and $\eta$ is the viscosity of the medium contacting the resonator.

Where the viscoelastic properties of the system are negligible or remain constant through the measurements, the surface mass density can be measured using a simplified expression that can be used for the loading causing the resonant frequency change up to 5% (approx. 4.5 mg/cm$^2$):

$$\rho_s = -C\Delta f_0$$

where C is determined by calibration and is typically equal $1.77 \times 10^{-5}$ mg/(sec cm$^2$ Hz) for a 5 MHz quartz crystal.

However, as discussed herein, the piezoelectric microbalance described in the foregoing references is unsuitable for testing calcium oxalate solutions as it does not provide the necessary conditions for the calcium oxalate crystals to precipitate on the surface of the microbalance. Consequently, a need still exists for methods of measuring the calcium oxalate scale forming tendencies of solutions under conditions at which calcium oxalate scale forming behavior is exhibited.

SUMMARY OF THE INVENTION

We have discovered that a metal-plated quartz-crystal microbalance can be used to provide the necessary conditions for the calcium oxalate crystals to precipitate on the surface of the microbalance, in particular by controlling the solution pH proximate to the surface of the microbalance by applying an appropriate electric polarization to the metal surface (the working electrode).

However, not any material can be used for plating the quartz crystal microbalance. Thus, piezoelectric microbalances utilizing traditional gold-coated crystals cannot be used to test calcium oxalate scale inhibitors as intensive hydrogen evolution is observed at the potential that provides for the near-surface pH suitable for oxalate scale formation. This hydrogen evolution interferes with and often completely precludes deposition of calcium oxalate scale on the microbalance.

Also, the test solution should have a proper pH and concentration of calcium oxalate. The solution pH should be low enough to provide for full solubility of the constituents. However, pH's less than 2 may be too low for an electrochemical polarization to produce the pH increase at the quartz microbalance sufficient to precipitate calcium oxalate from the solution while avoiding the evolution of hydrogen bubbles. On the other hand, pH's higher than 3 may not provide for the concentration of calcium and oxalate ions in the bulk solution sufficient for a reasonable deposition rate and rapid completion of the test.

Moreover, the surface activities of the inhibitors as well as the adsorption properties of the deposition interface depend on the pH. In order to keep the screening conditions the same for various solutions an actual knowledge of the pH in the vicinity of the microbalance working electrode is required.

We have developed a method and apparatus for testing potential calcium oxalate scale inhibitors and the capacity of industrial and biological solutions to form calcium oxalate deposits that utilizes a controlled change of the pH in an oxygen-saturated acidic test solution near the deposition substrate represented by the working electrode of a quartz crystal microbalance (QCM).

Accordingly, in its principal embodiment, this invention is directed to a method of measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is controlled electrochemically at from about 3.5 to about 9 and wherein the working electrode is coated with or made of a conductive material on which the intensive evolution of hydrogen gas proceeds at potentials more negative than necessary to achieve a pH of 3.5–9 proximate to the microbalance.

In another aspect, this invention is directed to method of measuring the effectiveness of calcium oxalate scale inhibitors comprising a) measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution. wherein the pH of the solution proximate to the microbalance is controlled electrochemically at from about 3.5 to about 9 and wherein the working electrode is coated with or made of a conductive material on which the intensive evolution of hydrogen gas proceeds at potentials more negative than necessary to achieve a pH of 3.5–9 proximate to the microbalance;

b) adding a calcium oxalate scale inhibitor to the solution; and c) re-measuring the rate of deposition of calcium oxalate scale from the solution on to the quartz crystal microbalance.

In another aspect, this invention is directed to an apparatus for measuring the calcium oxalate scale forming propensity of a continuously flowing solution having a pH of from about 2 to about 3 comprising a quartz crystal microbalance having a top side comprising a working electrode for exposure to the solution and a bottom side isolated from the solution, wherein the pH of the proximate to the microbalance is controlled electrochemically at from about 3.5 to about 9 and wherein the working electrode is coated with or made of a conductive material on which the intensive evolution of hydrogen gas proceeds at potentials more negative than necessary to achieve a pH of 3.5–9 proximate to the microbalance.

In another aspect, this invention is directed to apparatus for measuring the calcium oxalate scale forming propensity of a continuously flowing solution having a pH of from about 2 to about 3 comprising a measurement cell with stirring means and mounted in the measurement cell:

a) a quartz crystal microbalance having a top side comprising a working electrode for exposure to the solution and a bottom side isolated from the solution;

b) a surface pH-measuring module for exposure to the solution, the pH-measuring electrode assembly comprising a mesh electrode laid over a pH electrode wherein the mesh is made of the same material as the working electrode of the microbalance;

c) two reference electrodes for exposure to the solution; and d) two counter electrodes for exposure to the solution, wherein the quartz crystal microbalance and the surface pH-measuring module are mounted horizontally oppositely oriented, the two counter electrodes are mounted vertically and located each at an equal distance and downstream from the quartz crystal microbalance and the surface pH measuring module and the reference electrodes are mounted vertically and located each at an equal distance and downstream from the each of the counter electrodes and wherein the working electrodes of the surface pH measuring module and the quartz crystal microbalance are coated with or made of a conductive material on which the intensive evolution of hydrogen gas proceeds at potentials more negative than necessary to achieve a pH of 3.5–9 proximate to the microbalance.

The method of this invention simulates calcium oxalate scale formation from calcium and oxalate ion-containing solutions under conditions wherein the solution pH is raised above the salt solubility limit, with the solution chemistry providing a characteristic rate of precipitation. The solution pH increase is created electrochemically and controlled in-situ in the vicinity of a metal-plated quartz crystal microbalance which serves as a nucleation plate for the scale crystals.

The method and apparatus of this invention are useful for benchtop laboratory work or, in a portable form, for on-site process control. The method allows reliable and prompt testing of potential calcium oxalate scale inhibitors in both model and real solutions. It is reproducible, sensitive and has broader applications than known techniques that suffer from interference of additional components present in industrial solutions. This method allows specifically characterizing the ability of scale inhibitors to prevent calcium oxalate crystal growth and when used in conjunction with conventional chemical tests allows comprehensive characterization of the properties of calcium oxalate scale inhibitors.

In addition to testing industrial solutions, this method can be applied to biological solutions to characterize their tendency to form calcium oxalate deposits. It has a great potential for medical applications such as urine tests for susceptibility to kidney stone formation and monitoring and screening of potential pharmaceutical remedies.

The method and apparatus of this invention can also be utilized for measuring the inorganic scale-forming propensity of any aqueous solution where solubility of the scale is pH-dependent, including calcium carbonate; calcium salts of organic acids; magnesium hydroxide; and the like.

DETAILED DESCRIPTION OF THE INVENTION

Figure 1:
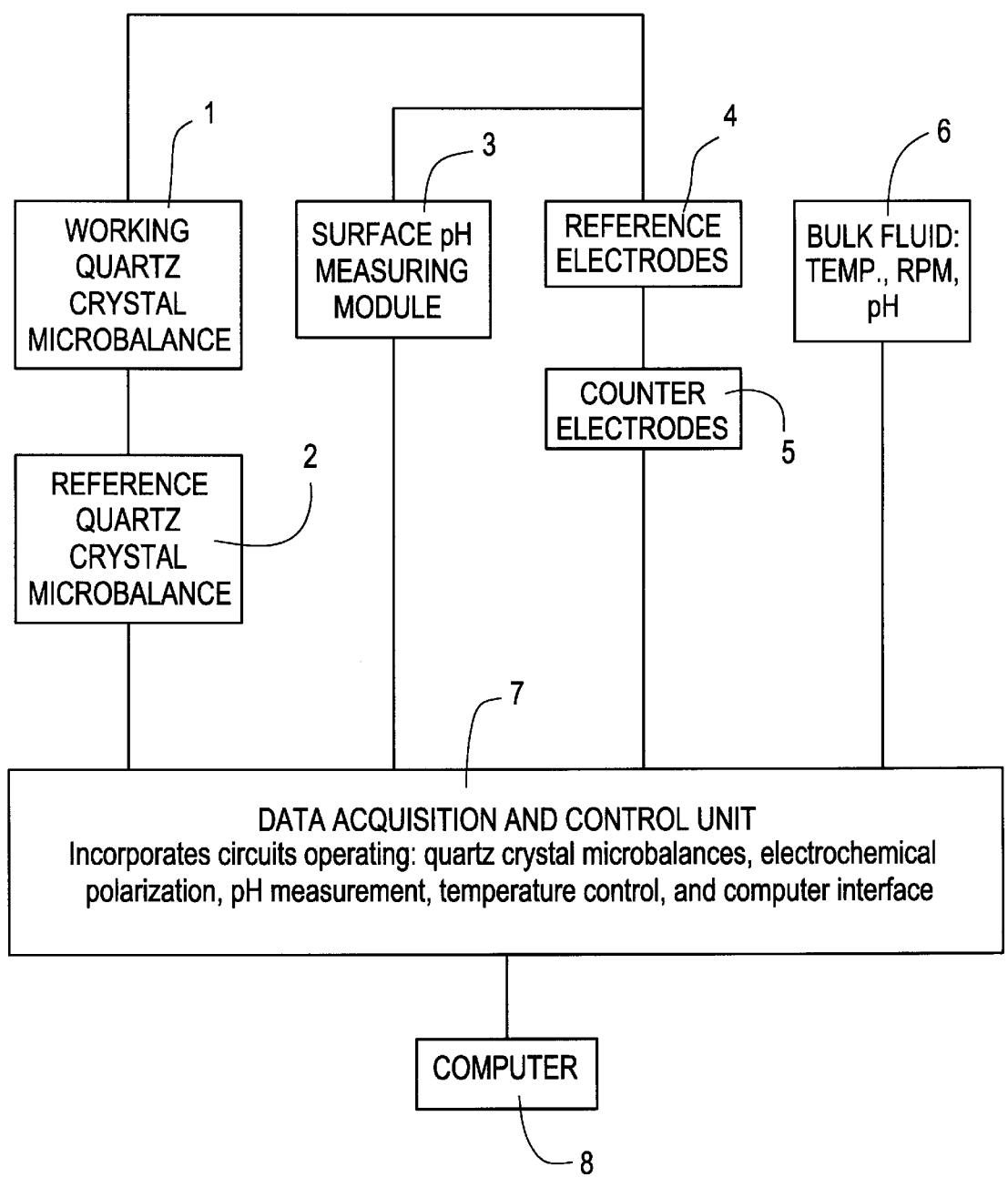
FIG. 1 is a block diagram of an apparatus of this invention for measuring the rate of calcium oxalate scale growth in a solution that includes a working quartz crystal microbalance (1), a reference quartz crystal microbalance (2), a surface pH measuring module (3), reference (4) and counter (5) electrodes, means (6) for controlling and measuring bulk solution temperature, pH, and solution flow, a data processing and control unit (7) connected to an external computer (8).

This method exploits precipitation of calcium oxalate from acidic solutions containing calcium and oxalate ions when the solution pH is raised. The rate of precipitation is measured with a sensitive quartz crystal microbalance in the vicinity of which a pH increase is generated and controlled electrochemically. This method utilizes an electrochemical set-up with a cell in which a continuous (constant for a given experimental series) flow of the test solution is established relative to the surface of the quartz crystal microbalance, wherein the test solution has a pH sufficiently high for electrochemical polarization to produce calcium oxalate deposition and sufficiently low to dissolve the oxalate salt in the solution.

The quartz crystal microbalance is a piezoelectric resonator connected to a measuring and driving circuit. The resonator is a quartz crystal plate with evaporated electrodes on its sides used for the connections. One of the resonator sides (the top or fluid side) with its electrode (the working electrode) is immersed in the test solution and the other side (the bottom or contact side) is left to the air to avoid shunting the resonator through the solution. When negative (cathodic) electrical polarization is applied to the working electrode, water and dissolved oxygen in the solution proximate to the working electrode are reduced with concomitant formation of hydroxyl ions resulting in a local pH increase and precipitation of calcium oxalate.

Sufficiently cathodic electricity also results in hydrogen ion reduction to hydrogen gas and formation of hydrogen bubbles. At low bulk pH the electrochemical potential of the hydrogen reaction is positive enough for hydrogen evolution to effectively hinder calcium oxalate precipitation by the bubbles partially blocking the working electrode and stirring the near electrode solution, preventing the necessary pH increase. Therefore the working electrode of the microbalance should be coated with or made of a conductive material on which the intensive evolution of hydrogen bubbles proceeds at potentials more negative than those necessary for calcium oxalate precipitation.

The rate of hydrogen evolution at a given potential largely depends on the electrode material used. Therefore, electrode materials with the highest possible hydrogen evolution overpotential, for which intensive hydrogen evolution proceeds at the highest possible cathodic polarization, should be utilized. Other consideration in selecting the electrode material include simplicity of handling, cost, and resistance to dissolution in an acidic medium. Representative materials having high hydrogen overpotential include silver; lead; cadmium; diamond-like thin film electrodes with or without implanted ions; silicides of titanium, niobium and tantalum; lead-selenium alloys; mercury amalgams (e.g., amalgamated copper); and the like. Silver is an especially preferred electrode material.

The other condition is that the test solution should have a proper pH and concentration of calcium oxalate. The solution pH should be low enough to provide for fall solubility of the constituents. However, pH's lower than 2 may result in the electrochemical induction producing an insufficient pH increase in the vicinity of the quartz microbalance to result in deposition of calcium oxalate from the solution. On the other hand, pH's higher than 3 may not provide for a sufficient concentration of calcium and oxalate ions in the bulk solution for a reasonable deposition rate and rapid completion of the test. Therefore, the pH range of from about 2 to about 3 is preferred for the test solution. Precipitation of calcium oxalate scale onto the surface of the quartz microbalance occurs when the pH of the solution proximate to the quartz microbalance (the local pH) is higher than about 3.5. A local pH of from about 3.5 to about 9 is preferred.

Figure 7:
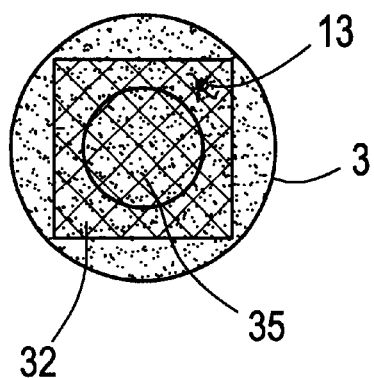
FIG. 7 is a top plan view of the surface pH measuring module (3).
Figure 8:
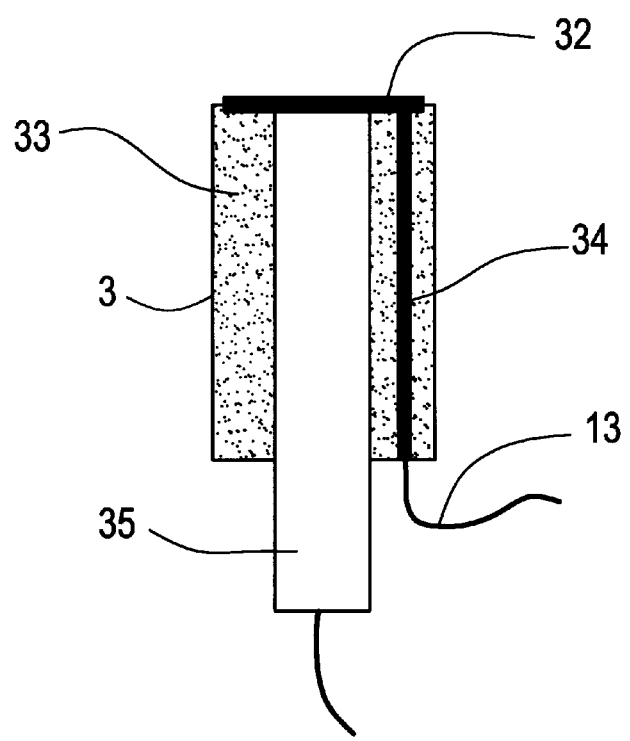
FIG. 8 is a cut away view of the surface pH measuring module (3).

In one embodiment of this invention, the pH measurement is accomplished using an auxiliary surface pH-measuring module (3) (SPH) comprising a mesh electrode (32) laid over a flat-tip combination pH electrode (35) as shown in FIGS. 7 and 8. The mesh should be as thin and dense as possible and made of the same material as the microbalance working electrode. Once subjected to the same test conditions, the mesh electrode allows approximating the surface pH conditions near the microbalance surface. In principle, other surface pH measuring set-ups can be utilized including but not limited to evaporated metal/metal oxide electrodes, microtip combination electrodes, and so on.

In another embodiment, the pH measurement is accomplished using a microtip combination electrode such as those available from Microelectrodes, Inc., Bedford, N.H. A microtip combination electrode is a miniaturized conventional pH electrode based on selective diffusion of protons though hydrogen ion sensitive glass, and the determination of potentials between the internal electrolyte and a silver/silver chloride reference electrode.

In another embodiment, the surface pH measurement is accomplished using a pH electrode evaporated on to the surface of the working quartz crystal microbalance (1). The working electrode (23) of the microbalance (1) has definite dimensions. The geometry of the electrochemical diffusion layer near the edge of this electrode presumes that the electrochemical induced pH change occurs not only in the vicinity above the electrode but also near the electrode edge in the lateral direction in the same plane. Therefore, if a small size pH sensor is placed near the edge and in the same plane as the microbalance working electrode the measurement of the near electrode pH is possible.

Thin-film metal oxide electrodes are preferred for such pH measurements. These materials are prepared by reactive sputtering of metals selected form the group of tungsten, platinum, palladium, ruthenium, and iridium metal targets in argon-oxygen atmospheres to produce a thin film several micron thick directly on the quartz crystal substrate (22).

As described above, a near electrode pH range from about 3.5 to 9 is preferred for the precipitation measurements. This preferred pH is achieved in the solution proximate to the working electrode while controlling its electrochemical polarization. Such control is accomplished using the surface pH measuring module. The module serves to establish the dependence of the near electrode pH on applied electrochemical polarization at given test conditions. Either potential or current control of electrochemical polarization can be used. The aforementioned dependence is obtained in a slow potential or current scan proceeding from low to high cathodic polarization. The current control can be advantageous from the hardware point of view because it does not require the use of reference electrodes and the compensation for solution resistance.

This dependence typically displays two regions of pH increase wherein the rate of calcium oxalate precipitation is proportional to the rate of hydroxyl ion production. The first region corresponds to oxygen reduction controlled by mass transport. The second region is located more cathodically and corresponds to the reduction of water to hydrogen. The oxygen reduction region and thus the center of the corresponding pH region on the polarization axis is preferable for the precipitation measurements producing the most intact deposit. In the second, more cathodic hydrogen region, two parts can be distinguished. In the beginning part of the hydrogen region only very small hydrogen bubbles evolve that are readily carried away by the solution flow. This part is characterized by the hydroxyl production rates higher than in the oxygen region and can also be used if faster completion of tests is required. The use of this part, however, requires tighter pH-polarization control to avoid slipping to a more cathodic range where larger bubbles of hydrogen gas would be produced, resulting in the loss of electric contact and disruption of the deposit.

The following procedures can be used to select appropriate control conditions from the dependence of the near electrode pH on the applied electrochemical polarization. In the case of current control, a slow scan of current from a near zero to a sufficiently large cathodic current (typically about 10 mA/cm2) is used to determine the current ranges producing the preferred pH range from 3.5 to 9 in the oxygen region or in the beginning of the hydrogen region. Consequently, the current is controlled in this range during the scale deposition. Preferably, a current of from about −0.05 to about −10 mA/cm$^2$ is applied to the working electrode.

In the case of potential control, a slow scan of potential from the open circuit potential to sufficiently large cathodic potential (typically 3 Volts vs. Ag/AgCl electrode) is used to determine the electrode potential ranges producing the preferred pH range from 3.5 to 9 in the oxygen region or in the beginning of the hydrogen region. Consequently, the potential is controlled in this range during the scale deposition. While using a stand alone surface pH measuring module in potential control scheme, it is necessary that the solution resistance between the reference and working electrodes of the surface pH module and the microbalance be the same or compensated. The resistance being the same is preferable because knowledge of a relative position of the potential on the pH-polarization dependence is sufficient to establish the required pH range in the near electrode solution. Preferably, a potential of from about −0.5 to about −2 V, more preferably from about −0.9 to about −1.5 V versus silver-silver chloride reference electrode is applied to the working electrode.

In either the potential or current control methods described above, if both the microbalance and surface pH module are used simultaneously a presetting of the desired test pH using a control "handle" at the beginning of the test is possible.

Figure 2:
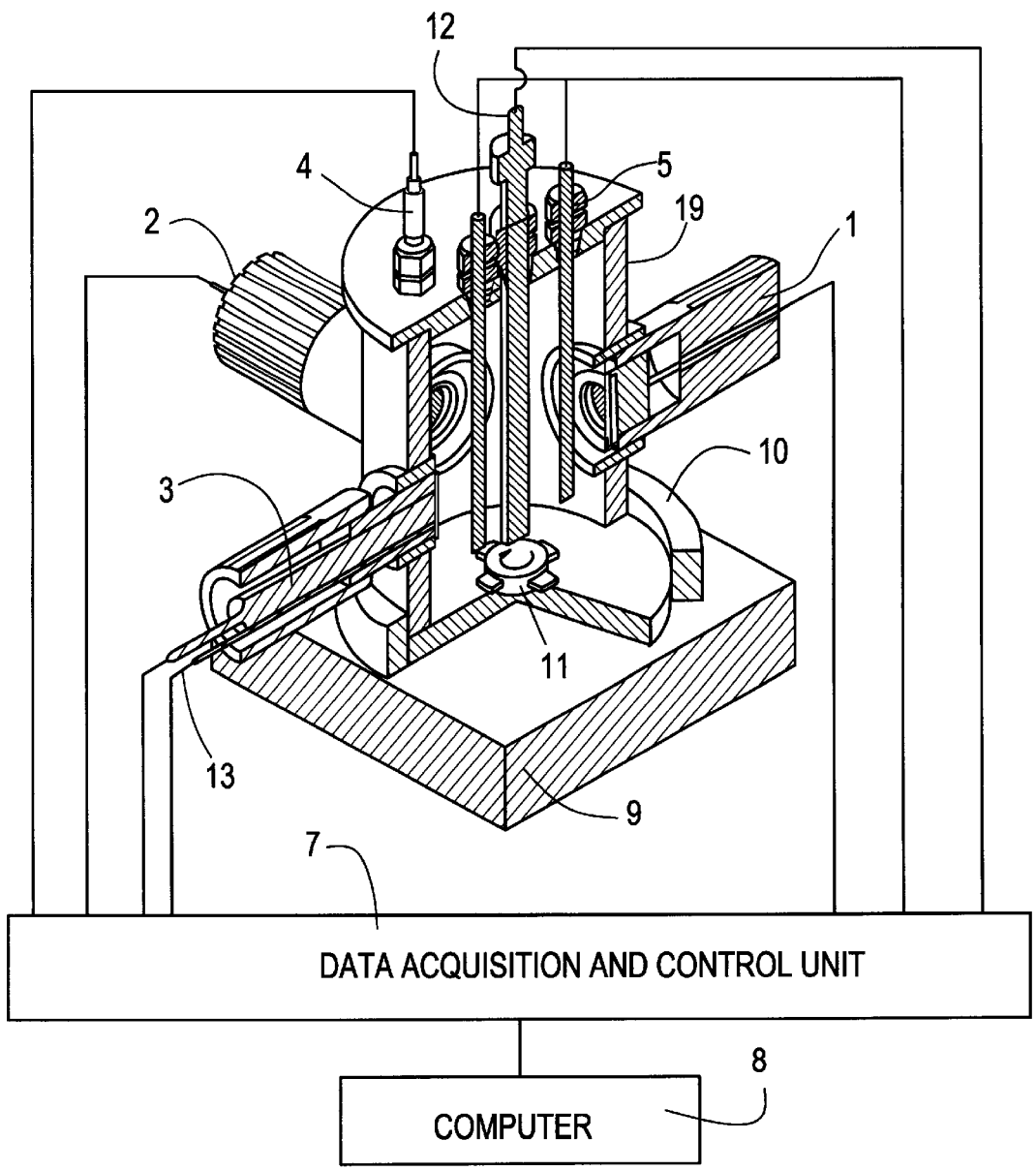
FIG. 2 is a partial cutaway view of the apparatus of this invention configured in batch mode.
Figure 3:
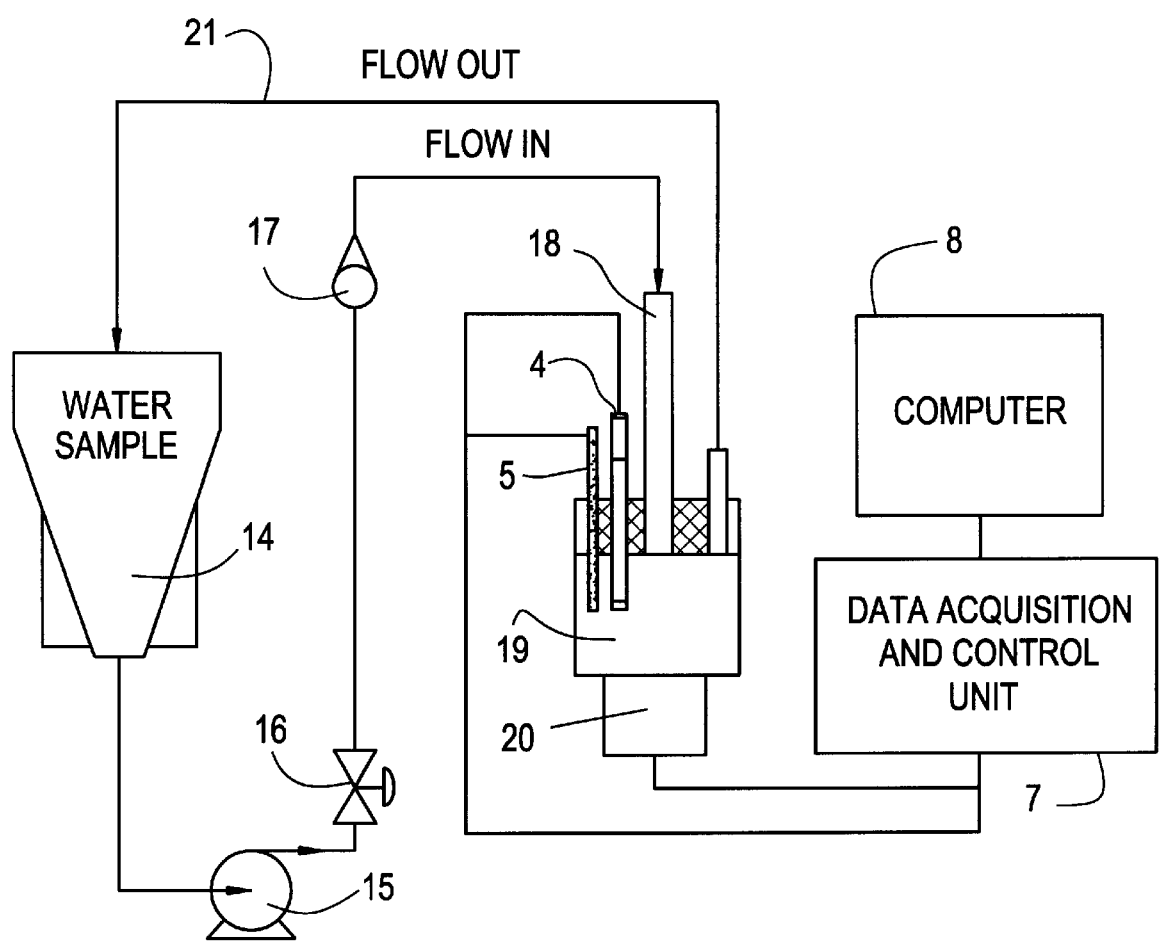
FIG. 3 is a schematic diagram of the apparatus of this invention configured as a continuous flow system.

Embodiments of the apparatus of this invention are illustrated in FIGS. 1–3.

A block diagram of an embodiment of the apparatus of this invention is shown in FIG. 1. The apparatus consists of a working quartz crystal microbalance (1), optionally a reference quartz crystal microbalance (2), a surface pH measuring module (3), reference (4) and counter (5) electrodes, means (6) for controlling and measuring bulk solution temperature, solution flow and pH, and a data processing and control unit (7) connected to an external computer (8).

Calcium oxalate deposition occurs at the working microbalance (1) when the polarization reaches the level generating the required pH in the near-electrode layer of the solution. Bulk parameters of the solution such as viscosity, conductivity and bulk pH may change during the experiment. The reference microbalance (2) is used to eliminate the effect of such possible changes on the experimental results. The reference microbalance (2) is not polarized and therefore calcium oxalate does not deposit on its surface. Because the reference (2) and working (1) microbalances are immersed in the same solution, the crystal resonant frequency change due to the deposit accumulation can be readily separated.

The data acquisition and control unit (7) executes experimental procedures and relays the experimental data to an external computer (8). The computer software controls the experiment setup and data acquisition and processes and plots the data. The programmed parameters are: electrochemical polarization (or, in one of possible embodiments, required surface pH), compensation for solution resistance, temperature, and flow of the solution (a flow rate in a continuous flow system or a rotation speed in a batch system). The external computer processes and stores the experimental data while displaying the test parameters and the deposition graphs (deposit amount and rate) in real time.

The measurement cell (19) is configured in a three-electrode arrangement using the working electrode (23) of the quartz crystal microbalance (1), reference (4), and counter (5) electrodes. The counter electrodes (5) are electrolytically connected to the bulk fluid and capable of applying a uniform electric field to the fluid side electrode (23) of the working microbalance (1) and to the surface pH module (3). The counter electrodes (5) are manufactured from graphite or other resistant materials readily apparent to those of skill in the art such as platinum, stainless steel, and the like.

The reference electrodes (4) measure the potentials of the working surfaces of the quartz crystal microbalance (1) and surface pH module (3). Silver-silver chloride reference electrodes are preferred. The reference electrodes (4) are located in the fluid, preferably as close as possible to the working electrode (23) of the quartz crystal microbalance (1) or the surface pH measuring module (3). However, the reference electrodes may not be necessary for a current control (galvanostatic) operation. If the electrochemical system can compensate for the potential drop on the solution resistance between the working and reference electrodes the distance between them may be larger.

In principle, the apparatus of this invention can utilize any electric source capable of supplying to the working electrode a polarization of suitable magnitude, polarity and stability. The electrical conditions established in the circuits can be controlled and measured using the equipment commonly used by those skilled in the art.

The apparatus of the present invention also includes means (6) for measuring and controlling the bulk fluid temperature, pH, and flow of the test solution.

A steady flow of the bulk liquid past the working (1) and reference (2) quartz crystals and the surface pH module (3) is accomplished using a suitable stirring device such as an impeller, a mechanical paddle stirrer, or a magnetic stirbar in a batch system or a water pump in a continuous flow system. By "steady," a relatively constant flow is intended. That flow may be either laminar or turbulent, with flow dynamics kept optimal for calcium oxalate precipitation and as close as practical to that of the simulated system.

The temperature of the fluid is controlled using any suitable thermal regulating means including, but not limited to, a cooler or heater disposed in the bulk liquid. The temperature of the bulk liquid is measured by a thermocouple connected to a controller. The temperature of the bulk liquid as measured by the thermocouple can be maintained constant or be varied, as much as is practical to simulate the desired system.

The apparatus of this invention may be operated as a batch system as shown in FIG. 2 or a continuous flow system as shown in FIG. 3. Both the batch and continuous flow systems utilize the same working microbalance (1) and surface pH measuring module (3) shown in FIGS. 5–8. The measurement cells are made of chemically resistant solid plastic (e.g., PVC or/and acrylic).

In the batch system setup shown in FIG. 2, the cell contains working (1) and reference (2) microbalances, the surface pH module (3) with its working electrode (32), two reference electrodes (4) (one of the reference electrodes is not shown due to the drawing section), two counter electrodes (5), a Teflon-coated cartridge heater (12), a temperature sensor (not shown) and a stirbar (11). The cell is placed on a plate of a precisely regulated magnetic stirrer (9). The data acquisition and control unit (7) incorporates circuits operating the quartz crystal microbalances, electrochemical polarization, pH measurement, temperature control and the interface to computer (8).

In the batch system the surface pH measuring module (3) and working microbalance (1) are used either consecutively or concurrently. In the latter case, an on-line adjustment of the polarization to reach the target pH on the surface of the microbalance is possible.

The measurement cell (19) is equipped with two microbalance assemblies: the working microbalance (1) is used for deposition measurements and the reference microbalance (2) (no polarization applied) is used for the baseline subtraction if solution properties such as viscosity and density change during the experiment. This arrangement is also helpful when the solution is naturally precipitating such as when suspended fibers or particles are present.

In the continuous flow system shown in FIG. 2, the test solution is stored and thermally conditioned in a glass or plastic funnel (14). Pump (15) delivers the solution from the funnel (14) through valve (16) controlling the flow and flowmeter (17), and further through the inlet channel (18) into the measurement cell (19). The solution exits the cell through tubing (21). Changes in the continuous flow system may be made to utilize an external input of test solution such as from a side stream of industrial process.

Number (20) in FIG. 3 represents a position in the measurement cell (19) at which either a surface pH measuring module (3) or the quartz crystal microbalance assembly (36) can be attached to the measurement cell (19).

The measurement cell (19) contains reference (4) and counter (5) electrodes. Connections between measurement cell (19), pump (15) and funnel (14) are preferably made using plastic tubing. The working microbalance (1), reference (4) and auxiliary (5) electrodes are connected to a data acquisition and control unit (7) that incorporates circuits operating the working microbalance (1), surface pH module (3) one or more electrochemical potentiostats and the computer (8).

Initially, optimal pH conditions are determined with the surface pH module (3) installed. Then the quartz microbalance assembly (36) is installed for measurement of scale forming capacity. In the first case, the mesh electrode (32) of the surface pH module (3) is connected to the same electrochemical system and subjected to the same test conditions as the working electrode (23) of microbalance (1). Both surface and bulk pH in the system are measured using the surface pH measuring module (3) connected to a pH-reading circuit in the data acquisition and control unit (7).

In another aspect of this invention, the continuous flow cell shown in FIG. 3 is modified by installing a working microbalance (1), surface pH module (3) and a branched inlet (18) in measurement cell (19) to permit on-line adjustment of the polarization to reach the target pH on the surface of the microbalance (1) as describe above for the batch system.

Figure 4:
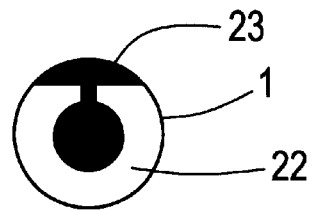
FIG. 4 is a top plan view of the quartz sensor of the quartz crystal microbalance (1).
Figure 5:
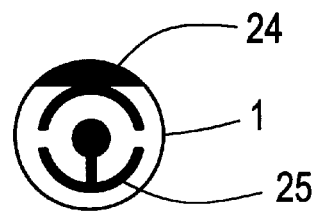
FIG. 5 is a bottom plan view of the quartz sensor of the quartz crystal microbalance (1).

Preferred configurations of the quartz crystal microbalance (1) and quartz crystal microbalance assemble (36) are shown in FIGS. 4 and 5. In this embodiment, the mass sensing element of the piezoelectric microbalance is an AT cut quartz crystal (22) with evaporated electrodes (23), (24), and (25). Electrode (23) is the working electrode as it is immersed into the tested fluid during measurements.

Working electrode (23) wraps around the edge of the top or fluid side of the crystal (22) to its bottom side to form contact (24) as shown in FIG. 5. The bottom side of the quartz crystal (22) also includes a second excitation electrode (24) with contact (25). The contacts (24) and (25) provide electrical connections with the microbalance operating circuit in the data acquisition and control unit (7) by way of connecting wires.

Figure 6:
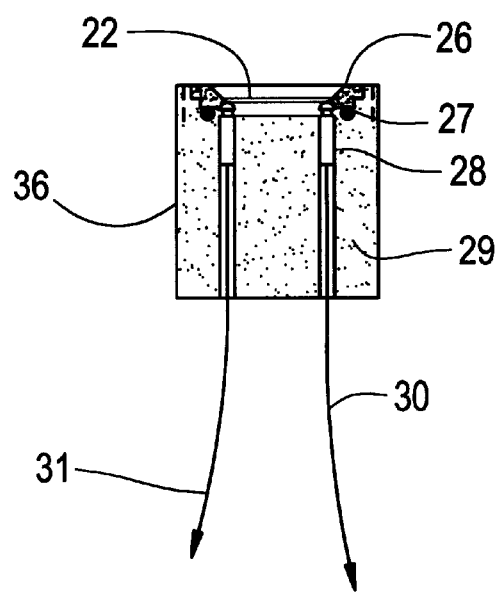
FIG. 6 is a cut away view of the quartz crystal microbalance assembly (36).

The quartz crystal microbalance assembly (36) is shown in FIG. 6. The quartz crystal (22) is sealed in an aperture of a constant flow or stationary cell. A retainer ring (26) and at least one O-ring (27) ensure that only the top side of the quartz crystal (22) is exposed to the test liquid and that the bottom side of the crystal is exposed only to air. Spring-loaded contacts (28) operatively connect the connecting leads (30) and (31) respectively to the crystal electrodes (23)

and (25). The leads are then connected to the microbalance operating circuit in the data acquisition and control unit (7).

The top or fluid side of the preferred surface pH measuring module (3) of this invention is shown in FIGS. 7 and 8. In this embodiment, a flat-bottom, upside-down mountable combination pH electrode (35) is fixed coaxially in a plastic cylinder (33) in such a way that the flat sensing surface of the electrode is in direct contact with a mesh (32) made of the same material as the microbalance electrode (23) and attached to the top of the plastic cylinder.

Maximizing the number of apertures per inch in mesh (32) leads to a better simulation of the microbalance working electrode. Variation of this parameter can be achieved by using mesh as thin and dense as practically available. In a preferred embodiment, the mesh is made of double-layer (45° turn) 50-mesh silver gauze woven from 0.0764-mm wire, flattened in a 25,000 kg press.

As shown in FIG. 8, the flat mesh (32) is connected to the electrochemical circuit in the data acquisition and control unit (7) using a wire (13) passing through an eccentric channel (34) in the plastic cylinder (33). Both the wire (13) and pH electrode (3) are tightly sealed in the corresponding channels of cylinder (33). The pH electrode (35) is connected to the pH reading circuits in the data acquisition and control unit. With the thickness of mesh (32) less than the electrochemical diffusion layer the device allows measuring the pH near the polarized electrode surface, thus simulating the environment near the surface of the working quartz microbalance. During the pH measurements, the surface pH module (3) is either used simultaneously with the working microbalance (1) as shown in FIG. 2 or is mounted in place of the working microbalance (1) as shown in FIG. 3. The same polarization is applied to the mesh electrode (32) of the surface pH module (3) and the working electrode of the quartz microbalance (1).

As discussed herein, optimal results using the method of this invention are achieved when the bulk solution pH is from about 2 to about 3 and the solution contains an optimized concentration of calcium and oxalate ions, preferably a combined concentration of greater than about 20 milligram per liter. Therefore, the efficiency of the testing process can be increased by using model solutions having the proper pH and calcium and oxalate ion concentrations, the model solutions being prepared prior to introduction into the measurement cell of the apparatus. These model solutions may be prepared by adjusting the pH and calcium and oxalate ion concentrations of process water or by preparing fresh solutions by mixing water, aqueous acid such as aqueous HCl and sources of calcium and oxalate ions such as sodium oxalate and calcium chloride dihydrate. For screening calcium oxalate scale inhibitors, a pre-determined amount of one or more inhibitors may be added to the model solution.

Accordingly, in another aspect, this invention is directed to a model solution prepared by adding acid and calcium and oxalate ion to process water such that the pH of the solution is from about 2 to about 3 and the combined concentration of calcium and oxalate ions is greater than 20 milligram per liter.

In another aspect, this invention is directed to a model solution prepared by mixing water, acid, and calcium and oxalate ions such that the pH of the solution is from about 2 to about 3 and the combined concentration of calcium and oxalate ions is greater than 20 milligram per liter.

The foregoing may be better understood by reference to the following Examples which are presented for purposes of illustration and are not intended to limit the scope of this invention.

EXAMPLE 1

The use of the method and apparatus of this invention to measure the effectiveness of calcium oxalate scale inhibitors in Kraft pulp bleach plants is described below. It is understood that the following is illustrative of a single application of this invention and is not intended to be limiting.

Pulp produced by the Kraft process is normally bleached in a multistage sequence to obtain the desired brightness and strength. The main objectives of pulp bleaching are to increase the brightness of the pulp and to make it suitable for the manufacture of printing and tissue grade papers by removal or modification of lignin and its degradation products of the unbleached pulp. The bleaching of chemical pulp is accomplished by a series of treatments involving chlorine dioxide, caustic, hydrogen peroxide, and other bleaching agents. The bleaching of chemical pulp normally begins with the first stage chlorine dioxide. The bleaching of pulp is done through chemical reactions of bleaching agents with the lignin and coloring matter of the pulp under different conditions of temperature, time, concentration, and pH.

Calcium oxalate is a difficult problem to control that can impair the performance of stock pipelines, washing filters, filtrate tanks, refiner plates, and heat exchangers. The formation of these deposits is a result of relatively high concentration of calcium oxalate in process equipment operating in the pH range of 2–8. The removal of this material is difficult and results in costly downtime.

The source of calcium oxalate in pulp bleaching operations is ultimately due to the wood. Calcium is introduced into the pulp mill principally from the wood, although some calcium may also be introduced into the process from the mill's fresh water and cooking liquor (sodium hydroxide and sodium sulfide). Oxalic acid is formed during pulping and bleaching but is also present in native wood. The precipitation of calcium oxalate is strongly dependent upon changes in temperature and pH.

A. The Apparatus

Rates of calcium oxalate scale formation from mill water in the presence of various commercially available inhibitors are measured using either the batch system as shown in FIG. 2 or the continuous flow system as shown in FIG. 3.

The composition of the mill water varies during different process stages. Therefore, for each mill water specimen a dynamic polarization experiment using the microbalance readings and surface pH measurements is used to determine the optimal pH and polarization of deposition. The flow rate of the test solution is adjusted to allow stationary hydrodynamic flow conditions that provide a balance between the oxygen supply to the electrode surfaces and nucleation and growth of calcium oxalate deposit.

In this example, the surface pH module is used to determine the pH change near the metal surface when the polarization is applied, for a series of polarization voltages typically in the range from 0 to −2 Volts versus silver-silver chloride reference electrode. The near electrode pH is measured in a 2 mV/sec potentiodynamic scan starting from the open circuit potential and going in the cathodic direction. The corresponding dependence of pH on polarization typically displays two regions of pH increase. The first region corresponds to the maximum rate of oxygen reduction controlled by mass transport. The second region is located at more cathodic potentials and corresponds to the reduction of water with hydrogen evolution. The oxygen reduction region and thus, the polarization corresponding to the center of the pH increase region is considered preferable for the precipitation measurements. This polarization is then used in all subsequent experiments using the quartz crystal microbalance as a deposit-measuring device.

The quartz microbalances used are 5 MHz silver coated polished quartz crystals (Maxtek, Inc., Torrance, Calif.).

The surface pH measuring module is a 50×35 mm PVC plastic cylinder with a 15-mm diameter channel drilled coaxially and a 2-mm diameter channel drilled eccentrically. A double layer (layers placed at 45° relative to each other) 15×15 mm 50-mesh silver gauze woven from 0.0764 mm wire (Alfa-Aesar, Ward Hill, Mass.) is flattened in a 25,000 kg press and attached to the top of the plastic cylinder with epoxy glue. The mesh electrode is connected to the electrochemical potentiostat in the data acquisition and control unit using a wire passing through the eccentric channel. A 15 mm diameter upside-down mountable flat-bottom combination pH electrode (Sensorex, Stanton, Calif.) is inserted into the coaxial channel so that its pH-sensing surface is flush with the silver mesh. The eccentric and coaxial channels are sealed watertight in the PVC cylinder. During the surface pH measurements the silver mesh is subjected to the same electrochemical polarization as the working electrode of the quartz microbalance.

The batch system and continuous flow system are configured as follows.

In the batch system, the working microbalance and the surface pH module are installed opposite to each other. Two counter electrodes are installed each at equal distance from the working microbalance and the surface pH module. The length of the counter electrodes is such that they pass through the cell top to bottom but still allow for stirbar rotation. The solution rotates clockwise. Each reference electrode is installed to the left of the working electrodes of the microbalance and surface pH modules at a distance of 1 cm from their central axis. Single junction silver-silver chloride reference electrodes in epoxy body with gel-filled reference (Sensorex, Stanton, Calif.) and high-density graphite counter electrodes (Perkin-Elmer, Oak Ridge, Tenn.) are used.

The batch and continuous flow systems are designed to be used with 1 L samples. The measurement cell is made of Plexiglas (batch system) and polyvinyl chloride (PVC) (continuous flow system). In the batch system, a digitally controlled 400S Stirrer and Teflon-coated 62-mm Spinstar stirbar (VWR, Chicago, Ill.) are used. In the continuous flow system, 1 cm internal diameter flexible PVC tubing is used to connect the unit with a centrifugal water pump, flowmeter, and a glass funnel that stores the test solution. The systems are connected to data acquisition and control unit.

The data acquisition and control unit is a microprocessor controlled electronic instrument that incorporates circuits operating the quartz crystal microbalances, pH measurements, and two electrochemical potentiostats (one for the working microbalance and one for the surface pH module). The unit is connected to an external IBM compatible computer. The computer software governs the experiment setup and data acquisition as well as processes and plots the data. The programmed parameters are: electrochemical polarization (or, in one of possible embodiments, required surface pH), temperature, and flow of the solution (a flow rate in a continuous flow system or a rotation speed in a batch system). The computer software processes and stores the experimental data while displaying the test parameters and the deposition graphs (deposition amount and rate) in real time.

Alternatively, the data acquisition and control unit described above may functionally be substituted with an electrochemical system such as CMS 100 (Gamry, Pa.), data acquisition card CYDAS-1602 (Cyber Research, Mass.) installed in a personal computer running a data acquisition software such as DASYLab (DasyTec, N.H.).

The measurements are performed at 25° C. and bulk pH 2.5–2.7 on the solutions containing (model solutions) or spiked with (bleach mill waters) 1 mM calcium oxalate. In a batch system, stirbar rotation speed of 400 rpm is maintained. In a continuous flow system, flow rate of 0.5 L/min is maintained.

B. Screening Of Calcium Oxalate Scale Inhibitors Using Model Solutions

A 1-mM (128-ppm) test solution of calcium oxalate is prepared as follows. Sodium oxalate (0.268 g) and calcium chloride dihydrate (0.294 g) are separately dissolved in 35 ml of 0.1 N HCl. The solutions are diluted to 100 ml each with deionized water, mixed under intense stirring, and the mixed solution is diluted to 2 L volume with deionized water with 0.1 N HCl added as needed to adjust the pH to 2.6. This solution is used as the control. In the tests, a potential inhibitor is added. The 700–900 ml solution samples are used with fresh portions used for each analysis.

C. Screening Of Calcium Oxalate Scale Inhibitors Using Mill Water

The test solutions contain 1-mM (128-ppm) of added calcium oxalate. Sodium oxalate (0.107 g) and calcium chloride dihydrate (0.118 g) are separately dissolved in 400-ml of mill water. 0.1 N HCl is added to the samples to maintain pH at about 2.5. The solutions are mixed and used as the control without an inhibitor, or with inhibitors for screening. It should be noted that actual mill water is typically characterized by the presence of a variety of organic materials that may act as natural scale inhibitors. The original mill water also contained visible dispersed cellulose fines. The experiments are repeated using the mill water vacuum-filtered through a glass filter to eliminate cellulose fines. The results agree well with those obtained previously using the original unfiltered mill water.

The system is flushed with deionized water immediately after the analysis. After each analysis of a model solution or mill water, the surface of the crystal is cleaned of the deposit with 0.1 N HCl (5–10 min) and washed with deionized water.

D. Calcium Oxalate Scale Inhibitor Screening Using The Batch And Continuous Flow System.

Various calcium oxalate scale inhibitors are screened using the method and apparatus of this invention. The tests are run at bulk pH 2.4–2.7 on filtered mill water (bleaching effluents) spiked with 1 mM calcium oxalate. No precipitation of calcium oxalate from the original mill water is observed, and the oxalate is introduced into the system before the experiments.

The behavior of the original mill water and of the mill water additionally passed through a glass filter is the same. Dispersed fine fibers apparently did not abrade the surface of the piezoelectric crystal, which is of vital importance for the use of this invention in the analysis of industrial liquors.

The scaling capacity of a solution is evaluated by the deposition rate observed at preset time intervals as well as by the total deposit accumulated by the end of the test. The percent inhibition is calculated as follows:

% Inhibition=100%×(Total deposit w/o inhibitor−Total deposit with inhibitor)/Total deposit without inhibitor.

The experimental data summarized below clearly distinguishes more and less effective inhibitor compositions. Thus, composition A decreases the rate of deposition dramatically and is the most effective in both mill water and in model solutions. The results are summarized in Tables 1–2 (batch system) and Table 3, 4 (continuous flow system).

In Tables 1–4, Sample A is a terpolymeric organic acid. Sample B is an alkaline solution of an acrylic polymer with a small amount of sulfur-containing inorganic salts. Sample C is a mixture of an acrylic polymer with an inorganic phosphorous salt. Composition D is a carbohydrate based inhibitor. Compositions A–D are available from Nalco Chemical Company, Naperville, Ill.

TABLE 1

Results of inhibitor screening in model solution (1 mM calcium oxalate)

| Sample, concentration of dry inhibitor | Deposition rate, mg/cm2/hour at reference time periods | | | Total deposit, mg/cm2 | % Inhibition |
|---|---|---|---|---|---|
| | 10 min | 20 min | 30 min | 30 min | |
| Control, 1 mM calcium oxalate | 0.38 | 0.45 | 0.43 | 0.146 | |
| A, 10 ppm | 0.10 | 0.14 | 0.18 | 0.028 | 80.8 |
| A, 40 ppm | 0.08 | 0.08 | 0.10 | 0.002 | 98.6 |
| B, 10 ppm | 0.22 | 0.36 | 0.44 | 0.105 | 28.1 |
| C, 10 ppm | 0.13 | 0.17 | 0.18 | 0.034 | 76.7 |

TABLE 2

Results of inhibitor screening in mill water (1 mM calcium oxalate added)

| Sample, concentration of dry inhibitor | Deposition rate, mg/cm2/hour at reference time periods | | | | Total deposit, mg/cm2 | % Inhibition |
|---|---|---|---|---|---|---|
| | 10 min | 20 min | 30 min | 40 min | 40 min | |
| Control, Mill water + 1 mM calcium oxalate | 0.49 | 0.58 | 0.5 | 0.39 | 0.261 | |
| A, 10 ppm | 0.10 | 0.10 | 0.11 | 0.10 | 0.010 | 96.2 |
| D, 10 ppm | 0.12 | 0.13 | 0.14 | 0.13 | 0.035 | 86.6 |

TABLE 3

Results of inhibitor screening in model solution (1 mM calcium oxalate)

| Sample, concentration of dry inhibitor | Deposition rate, mg/cm2/hour at reference time periods | | | Total deposit, mg/cm2 | % Inhibition |
|---|---|---|---|---|---|
| | 20 min | 40 min | 60 min | 60 min | |
| Control, 1 mM calcium oxalate | 0.45 | 0.40 | 0.38 | 0.310 | |
| A, 40 ppm | 0.03 | 0.10 | 0.15 | 0.052 | 83.2 |
| C, 40 ppm | 0.12 | 0.22 | 0.20 | 0.072 | 76.8 |
| B, 40 ppm | 0.20 | 0.35 | 0.40 | 0.199 | 35.8 |

TABLE 4

Results of inhibitor screening in mill water

| Sample, concentration of dry inhibitor | Deposition rate, mg/cm2/hour at reference time periods | | | Total deposit, mg/cm2 | % Inhibition |
|---|---|---|---|---|---|
| | 20 min | 40 min | 60 min | 60 min | |
| Control 0, Mill water, no calcium oxalate added | 0.05 | 0.04 | 0.04 | 0.001 | |
| Control, Mill water + 1 mM calcium oxalate | 0.50 | 0.51 | 0.49 | 0.434 | 83.2 |
| A, 40 ppm | 0.04 | 0.08 | 0.12 | 0.033 | 92.4 |
| C, 40 ppm | 0.62 | 0.70 | 0.62 | 0.570 | — |
| B, 40 ppm | 0.58 | 0.57 | 0.49 | 0.503 | — |

E. Screening of the Calcium Oxalate Scaling Capacity of Real Mill Waters Acquired from Various Hardwood D0 Process Stages The results of the use of the batch system for screening of the oxalate scaling capacity of real mill waters acquired from various D0 process stages are given in Table 5. Two sets of mill water, taken before and after the change in the operational procedure at the mill, are analyzed. The tests are performed on the original solutions and on the same solutions spiked with 1 mM calcium oxalate.

TABLE 5

Scale capacity screening of mill waters

| Sample | Deposition rate, mg/cm2/hour at reference time periods | | | | Total deposit accumulated, mg/cm2 |
|---|---|---|---|---|---|
| | 10 min | 20 min | 30 min | 40 min | 40 min |
| Mill water 1, pH 2.46 (before procedure change), no calcium oxalate | 0.08 | 0.11 | 0.10 | 0.10 | 0.026 |
| Mill water 1, pH 2.46 (before procedure change) + 1 mM calcium oxalate | 0.51 | 0.75 | 0.90 | 1.00 | 0.425 |
| Mill water 2, pH 2.25 (after procedure change) | 0.09 | 0.09 | 0.10 | 0.12 | 0.011 |
| Mill water 2, pH 2.25 (after procedure change) + 1 mM calcium oxalate | 0.48 | 0.65 | 0.67 | 0.70 | 0.332 |

What is claimed is:

1. A method of measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is controlled electrochemically at from about 3.5 to about 9 and wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance.

2. The method of claim 1 wherein the working electrode is made of or coated with one or more conductive materials selected from silver; lead; cadmium; diamond-like thin film electrodes with or without implanted ions; silicides of titanium, niobium and tantalum; lead-selenium alloys; and mercury amalgams.

3. The method of claim 1 wherein the working electrode is made of silver.

4. The method of claim 3 wherein the working electrode is made of titanium coated with silver.

5. The method of claim 1 wherein the pH of the solution proximate to the surface of the microbalance is controlled by applying to the working electrode a potential from about −0.5 to about −2.0 V versus silver-silver chloride reference electrode.

6. The method of claim 1 wherein the pH of the solution proximate to the surface of the microbalance is controlled by applying to the working electrode a cathodic current of from about −0.05 to about −10 mA/cm$^2$.

7. The method of claim 1 wherein the pH of the solution proximate to the surface of the microbalance is measured using a pH-measuring device selected from a microtip pH electrode and a pH electrode evaporated onto the surface of the quartz crystal microbalance.

8. The method of claim 1 wherein the solution having a pH of from about 2 to about 3 has a combined concentration of calcium and oxalate ions of greater than about 20 milligram per liter.

9. The method of claim 8 wherein the solution is a model solution prepared by adding acid and calcium and oxalate ion to process water such that the pH of the solution is from about 2 to about 3 and the combined concentration of calcium and oxalate ions is greater than 20 milligram per liter.

10. The method of claim 8 wherein the solution is a model solution prepared by mixing water, acid, and calcium and oxalate ions such that the pH of the solution is from about 2 to about 3 and the combined concentration of calcium and oxalate ions is greater than 20 milligram per liter.

11. A method of measuring the effectiveness of calcium oxalate scale inhibitors comprising a) measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is controlled electrochemically at from about 3.5 to about 9 and wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance;

b) adding a calcium oxalate scale inhibitor to the solution; and c) re-measuring the rate of deposition of calcium oxalate scale from the solution on to the quartz crystal microbalance.

12. An apparatus for measuring the calcium oxalate scale forming propensity of a continuously flowing solution having a pH of from about 2 to about 3 comprising a quartz crystal microbalance having a top side comprising a working electrode for exposure to the solution and a bottom side isolated from the solution, wherein the pH of the solution proximate to the microbalance is controlled electrochemically at from about 3.5 to about 9 and wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance.

13. The apparatus of claim 12 wherein the working electrode is made of or coated with one or more conductive materials selected from silver; lead; cadmium; diamond-like thin film electrodes with or without implanted ions; suicides of titanium, niobium and tantalum; lead-selenium alloys; and mercury amalgams.

14. The apparatus of claim 12 wherein the working electrode is made of silver.

15. The apparatus of claim 14 wherein the working electrode is made of titanium coated with silver.

16. An apparatus for measuring the calcium oxalate scale forming propensity of a continuously flowing solution having a pH of from about 2 to about 3 comprising a measurement cell with stirring means and mounted in the measurement cell:

a) a quartz crystal microbalance having a top side comprising a working electrode for exposure to the solution and a bottom side isolated from the solution;

b) a surface pH-measuring module for exposure to the solution, the pH-measuring electrode assembly comprising a mesh electrode laid over a pH electrode wherein the mesh is made of the same material as the working electrode of the microbalance;

c) two reference electrodes for exposure to the solution; and d) two counter electrodes for exposure to the solution, wherein the quartz crystal microbalance and the surface pH-measuring module are mounted horizontally oppositely oriented, the two counter electrodes are mounted vertically and located each at an equal distance and downstream from the quartz crystal microbalance and the surface pH measuring module and the reference electrodes are mounted vertically and located each at an equal distance and downstream from the each of the counter electrodes and wherein the working electrodes of the surface pH measuring module and the quartz crystal microbalance are coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance.

17. The apparatus of claim 16 wherein the stirring means is selected from an impeller, a mechanical paddle stirrer, and a magnetic rotator with a strirbar.

18. The apparatus of claim 17 wherein the working electrodes of the surface pH measuring module and the quartz crystal microbalance made of or coated with one or more conductive materials selected from silver; lead; cadmium; diamond-like thin film electrodes with or without implanted ions; suicides of titanium, niobium and tantalum; lead-selenium alloys; and mercury amalgams.

19. The apparatus of claim 17 wherein the working electrodes of the surface pH measuring module and the quartz crystal microbalance are made of silver.

20. The apparatus of claim 19 wherein the working electrodes of the surface pH measuring module and the quartz crystal microbalance are made of titanium coated with silver.

21. A method of measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is controlled electrochemically at from about 3.5 to about 9, wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance and wherein the pH of the solution proximate to the surface of the microbalance is measured using a surface pH measuring module comprising a mesh electrode laid over a pH electrode wherein the mesh is made of the same material as the working electrode.

22. A method of measuring the effectiveness of calcium oxalate scale inhibitors comprising
  a) measuring the calcium oxalate scale forming propensity of a continuously flowing solution having a pH of from about 2 to about 3 comprising measuring the rate of deposition of calcium oxalate scale from the solution on to a quartz crystal microbalance having a top side comprising a working electrode in contact with the solution and a second, bottom side isolated from the solution, wherein the pH of the solution proximate to the microbalance is controlled electrochemically at from about 3.5 to about 9, wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance and wherein the pH of the solution proximate to the surface of the microbalance is measured using a surface pH measuring module comprising a mesh electrode laid over a pH electrode wherein the mesh is made of the same material as the working electrode;
  b) adding a calcium oxalate scale inhibitor to the solution; and
  c) re-measuring the rate of deposition of calcium oxalate scale from the solution on to the quartz crystal microbalance.

23. An apparatus for measuring the calcium oxalate scale forming propensity of a continuously flowing solution having a pH of from about 2 to about 3 comprising
  i) a quartz crystal microbalance having a top side comprising a working electrode for exposure to the solution and a bottom side isolated from the solution; and
  ii) a surface pH measuring module comprising a mesh electrode laid over a pH electrode wherein the mesh is made of the same material as the working electrode,
wherein the pH of the solution proximate to the microbalance is controlled electrochemically at from about 3.5 to about 9 and wherein the working electrode is coated with or made of a conductive material on which the evolution of hydrogen gas does not interfere with the deposition of calcium oxalate onto the surface of the working electrode at the electrochemical polarization necessary to achieve a pH of 3.5–9 proximate to the microbalance.

* * * * *